United States Patent [19]

Samreth et al.

[11] Patent Number: 4,598,068

[45] Date of Patent: Jul. 1, 1986

[54] BENZYLPHENYL OSIDES, METHOD OF PREPARATION AND USE THEREFOR

[75] Inventors: Soth Samreth, Longvic; François Bellamy, Saulon La Rue; Jean-Bernard Chazan, Dijon, all of France

[73] Assignee: Societe de Recheres Industrielles, Paris, France

[21] Appl. No.: 632,009

[22] Filed: Jul. 18, 1984

[30] Foreign Application Priority Data

Jul. 20, 1983 [FR] France ................................ 83 11982

[51] Int. Cl.$^4$ ............................................. A61K 31/70
[52] U.S. Cl. ..................................... 514/25; 536/4.1; 536/18.1; 536/18.5
[58] Field of Search ................ 536/4.1, 18.1, 18.5, 536/55.2, 17.8, 18.7; 514/25

[56] References Cited

U.S. PATENT DOCUMENTS 3,884,906  5/1975  Van der Meer et al. .......... 536/18.7
4,432,973  2/1984  Picart ................................... 536/4.1

FOREIGN PATENT DOCUMENTS 0051023 10/1981 European Pat. Off. ............. 536/4.1

OTHER PUBLICATIONS

Levai et al., "Acta Chimica Academiae Scientiarum Hungaricae, Tomus 84 (1), pp. 99–107, 1975.
Kammerer et al., "Makromol. Chem." 182, 1351–1361, 1981.
Vol. 3, Comprehensive Organic Chemistry The Synthesis and Reactions of Organic Compounds.
Vol. 34 A Practical Synthesis of Tetraphenyleyclopentadiene from Tetracyclone Recorded Apr. 9, 1969.
Chem. Abst., vol. 82, No. 14, p. 468, No. 98327c, Apr. 1975.
Chem. Abst. vol. 95, No. 9, p. 831, No. 81409b, Aug. 1981.
Chem. Abst. vol. 90, No. 5, p. 8, No. 33707x, Jan. 1979.
Chem. Abst., vol. 86, No. 7, p. 21, No. 37568t, Feb. 1977.

Primary Examiner—Johnnie R. Brown
Attorney, Agent, or Firm—Martin P. Hoffman; Mitchell B. Wasson; Stewart L. Gitler

[57] ABSTRACT

The present invention relates, by way of new industrial products, to the benzylphenyl osides of the formula

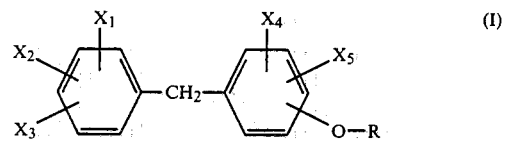

in which:

$X_1$, $X_2$, $X_3$, $X_4$ and $X_5$, which are identical or different, each represent a hydrogen atom, a halogen atom, a $C_1$–$C_4$ alkyl group, a $C_1$–$C_4$ alkyl group substituted by one or more halogen atoms (in particular a $CF_3$ group), an OH group, a $C_1$–$C_4$ alkoxy group, a $C_1$–$C_4$ alkoxy group substituted by one or more halogen atoms, a nitro group, a group NR'R" (in which R' and R", which are identical or different, each represent the hydrogen atom, a $C_1$–$C_4$ alkyl group or an acetyl group), a methylthio group, a methylsulfinyl group or a mesyl group, and R represents an ose radical chosen from the group comprising
 (a) the α-L-rhamnosyl radical,
 (b) non-hydrolyzable monosaccharide radicals and
 (c) non-hydrolyzable monosaccharide radicals in which the hydroxyl group on the carbon atom in the 2-position is replaced with an amine group, the hydroxyl and amine groups of the group R being capable of acetylation, and their addition salts in cases where at least one of the groups $X_1$, $X_2$, $X_3$, $X_4$, $X_5$ and R comprises a basic radical.

These new products are useful in therapy. They can be prepared by reducing the corresponding benzoylphenyl and α-hydroxybenzylphenyl osides.

10 Claims, No Drawings

BENZYLPHENYL OSIDES, METHOD OF PREPARATION AND USE THEREFOR

The present invention relates, by way of new industrial products, to the benzylphenyl osides of the formula I below, and their salts. It also relates to the method of preparation and the use in therapy of these new products.

It is known that it has been proposed in the past to use phenyl glycosides as agents possessing antiviral properties, cf., in this connection, the article by HIROSHI ARITA, Carbohydrate Research 62, 143–154 (1978).

It is also known that European Patent Application A-51,023 has already proposed benzoylphenyl and α-hydroxybenzylphenyl osides useful as ulcer inhibitors, platelet aggregation inhibitors, antithrombotics and cerebral oxygenators.

It has been found, surprisingly, that replacement of the CO and CHOH groups located between the two phenyl nuclei in the general formula of European Patent Application A-51,023 with a $CH_2$ group gives compounds of particular value as hypocholesterolemic and hypolipidemic agents, whereas the previously known benzoylphenyl oside and α-hydroxybenzylphenyl oside derivatives are devoid of hypocholesterolemic and hypolipidemic effects.

The new products according to the invention are chosen from the group comprising
(i) the benzylphenyl osides of the general formula

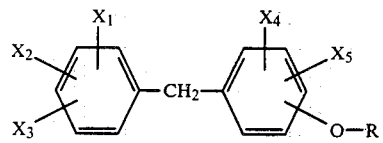

in which:
$X_1$, $X_2$, $X_3$, $X_4$ and $X_5$, which are identical or different, each represent a hydrogen atom, a halogen atom, a $C_1$-$C_4$ alkyl group, a $C_1$-$C_4$ alkyl group substituted by one or more halogen atoms (in particular a $CF_3$ group), an OH group, a $C_1$-$C_4$ alkoxy group, a $C_1$-$C_4$ alkoxy group substituted by one or more halogen atoms, a nitro group, a group NR'R" (in which R' and R", which are identical or different, each represent the hydrogen atom, a $C_1$-$C_4$ alkyl group or an acetyl group), a methylthio group, a methylsulfinyl group or a mesyl group [$-SO_2CH_3$], and R represents an ose radical chosen from the group comprising
(a) the α-L-rhamnosyl radical,
(b) non-hydrolyzable monosaccharide radicals and
(c) non-hydrolyzable monosaccharide radicals in which the hydroxyl group on the carbon atom in the 2-position is replaced with an amine group, the hydroxyl and amine groups of the group R being capable of acetylation; and
(ii) their acid addition salts in cases where at least one of the groups $X_1$, $X_2$, $X_3$, $X_4$, $X_5$ and R comprises a basic radical.

Regarding the structure of the formula I given above, the group —O—R can be in the ortho, meta or para position relative to the $CH_2$ group located between the two phenyl nuclei.

In the present context, the term "ose" which forms part of the definition of the radical R denotes any non-hydrolyzable elementary carbohydrate unit of the empirical formula $(CH_2O)_n$, i.e. on the one hand non-hydrolyzable monosaccharide carbohydrates and on the other hand α-L-rhamnose, which is a deoxyose derivative of the empirical formula $C_6H_{12}O_5$. Furthermore, according to the invention, the hydrogen atom of each hydroxyl group of the ose radical can be replaced with a $COCH_3$ group and the hydroxyl group on the carbon atom in the 2-position can be replaced with an amine group, which is itself capable of being substituted by a $COCH_3$ group.

Consequently, R represents in particular a glycosyl radical such as β-D-glucosyl, β-D-xylosyl, β-D-galactosyl, α-L-arabinosyl, β-D-glucosaminyl or α-L-rhamnosyl, it being possible, if appropriate, for the hydroxyl and amine groups to be substituted by an acetyl group.

The term "halogen atom" is understood here as meaning fluorine, chlorine, bromine and iodine atoms, the preferred halogens being fluorine, chlorine and bromine; among these, the halogens of greatest value from the therapeutic point of view are chlorine and bromine.

Among the compounds of the formula I which are preferred according to the invention, there may be mentioned, in particular, the derivatives in which $X_1$, $X_2$, $X_3$, $X_4$ and $X_5$, which can be identical or different, each represent H, Cl, Br, $CH_3$, $CF_3$, OH, $OCH_3$, $NO_2$, $NH_2$, $N(CH_3)_2$, $SCH_3$, $SOCH_3$ or $SO_2CH_3$ and R represents a radical chosen from the group comprising the α-L-rhamnosyl, β-D-glucosyl, β-D-xylosyl, β-D-galactosyl, α-L-arabinosyl and β-D-glucosaminyl radicals, in which, if appropriate, the OH and $NH_2$ groups can be acetylated.

The compounds of the formula I can be prepared by a method known per se, according to a classical reaction mechanism. The recommended method consists in reducing a compound of the formula

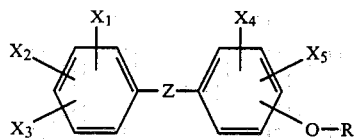

(in which Z is CO or CHOH and $X_1$, $X_2$, $X_3$, $X_4$, $X_5$ and R are defined as indicated above) by means of a reducing agent chosen from $NaBH_4$ and $KBH_4$, in trifluoroacetic acid.

The best embodiment of this method consists successively in (i) introducing the reducing agent into a mixture comprising the compound II and the trifluoroacetic acid, at a temperature below or equal to 0° C. and preferably between the solidification point of the reaction medium and 0° C., the reducing agent being in excess relative to the compound II, and (ii) when the said addition has ended, allowing the reaction to continue for 0.5 to 12 hours at a temperature of between 0° C. and 20° C., with stirring.

In practice, the reducing agent is introduced in small portions over at least 0.5 hour.

In the best embodiment given above, when Z is CHOH, at least 3 mol of reducing agent are used per mol of compound II, and when Z is CO, at least 6 mol of reducing agent are used per mol of compound II.

Furthermore, in order to solubilize the starting material II, the trifluoroacetic acid is advantageously used in association with a chlorinated solvent, in particular methylene chloride in a ratio $CF_3COOH/CH_2Cl_2$ of 1:2 v/v.

To obtain a compound of the formula I in which the radical R is not acetylated, it can be advantageous to reduce a compound of the formula II in which R is acetylated to give a compound I in which R is acetylated, the latter then being subjected to a deacetylation reaction, because (1) the acetylated derivative II is more soluble in the reaction medium than the non-acetylated derivative II, and
(2) each $COCH_3$ group attached to the radical R is not affected by the reduction reaction involving $NaBH_4$ or $KBH_4$.

The deacetylation of the group R is advantageously carried out by heating under reflux in a $C_1$–$C_3$ lower alcohol, in the presence of the corresponding metal alcoholate. Preferably, the lower alcohol used here will be methanol and the metal alcoholate will be sodium methylate or magnesium methylate.

According to the invention, a therapeutic composition is proposed which contains, in association with a physiologically acceptable excipient, at least one compound chosen from the group comprising the products of the formula I and their non-toxic addition salts.

The compounds of the formula I are useful in therapy as hypocholesterolemic and hypolipidemic agents. They are useful in the treatment of hypercholesterolemia and hyperlipidemia and in particular in the treatment of lipid excesses.

The common property of the compounds of the formula I is the hypocholesterolemic and hypolipidemic effects; in addition to this common property, some compounds, in particular the product of Example 1 below, also have beneficial antithrombotic effects.

Further characteristics and advantages of the invention will be understood more clearly on reading the preparation examples below, which are given by way of illustration without in any way implying a limitation.

PREPARATION I

Preparation of 4-(4-nitrobenzyl)phenyl β-D-xylopyranoside (Example 1; code no. 646)

11 g (0.0291 mol) of 4-(4-nitro-α-hydroxybenzyl)phenyl β-D-xylopyranoside are dissolved in 100 ml of anhydrous $CH_2Cl_2$ and 50 ml of trifluoroacetic acid under a stream of nitrogen. 3 g (0.0773 mol) of sodium tetraborohydride are added cautiously in small fractions at 0° C. The addition takes about 45 minutes.

Stirring is continued at this temperature until the starting material has completely disappeared as determined by TLC [eluent: $CHCl_3/CH_3OH$ 1:1 v/v], which takes about 0.5 hour. The reaction medium is then poured onto ice and the precipitate formed is filtered off. This precipitate is washed with cold water until the pH of the washings is neutral, and recrystallized from isopropanol. 10.2 g (yield: 97%) of the expected product are thus collected.

Melting point=166° C.
$[\alpha]_D^{20} = -21°$ (c=0.5 g/liter; methanol)

PREPARATION II

Preparation of 4-(4-chlorobenzyl)phenyl 2,3,4-tri-O-acetyl-β-D-xylopyranoside (Example 44)

7.1 g (0.014 mol) of 4-(4-chlorobenzoyl)phenyl 2,3,4-tri-O-acetyl-β-D-xylopyranoside, and then 100 ml of anhydrous methylene chloride and 58 ml of trifluoroacetic acid, are introduced at 0° C. into a 250 ml round-bottomed flask fitted with a powerful stirrer and placed under a stream of nitrogen. With the temperature kept at 0° C., 3.5 g (0.09 mol) of sodium tetraborohydride are added cautiously in small portions. This addition takes approximately 2 hours. When the addition has ended, the mixture is stirred at 0° C. for about 3 hours until the starting material has completely disappeared as determined by TLC [eluent: $CH_3C_6H_5/CH_3CO_2C_2H_5$ 2:1 v/v]. The mixture is then hydrolyzed on ice and extracted several times with methylene chloride. The organic phase thus obtained is washed with water, then with a saturated solution of sodium bicarbonate and finally with water until the pH of the washings is neutral. This organic phase is dried over anhydrous sodium sulfate and filtered and the filtrate is then evaporated under reduced pressure at 30°–40° C. After crystallization from methanol, 6.5 g (yield: 94%) of the expected product are obtained pure.

Melting point=101° C.
$[\alpha]_D^{20} = -19°$ (c=0.5 g/liter; ethyl acetate)

PREPARATION III

Prepartion of 4-(4-chlorobenzyl)phenyl β-D-xylopyranoside (Example 9; code no. 940)

5.5 g (0.0015 mol) of 4-(4-chlorobenzyl)phenyl 2,3,4-tri-O-acetyl-β-D-xylopyranoside (product of Example 44 obtained according to Preparation II above) are dissolved in 150 ml of methanol, under a stream of nitrogen, at ambient temperature (15°–20° C.). 1.8 ml of approximately 7% w/v sodium methylate solution are added and the reaction medium is then stirred at ambient temperature for 2 hours. Amberlite IR 120H resin is then added, the pH of the alcohol solution being monitored. When neutral pH is reached, the resin is filtered off, the filtrate is evaporated under reduced pressure at 30°–40° C. and the product obtained is recrystallized from an ethanol/water mixture 1:1 v/v. This gives 2.5 g (yield: 62%) of the expected product.

Melting point=149° C.
$[\alpha]_D^{20} = -25°$ (c=0.5 g/liter; $CH_3OH$)

PREPARATION IV

Preparation of 4-(3-nitrobenzyl)phenyl 2,3,4-tri-O-acetyl-β-D-xylopyranoside (Example 37)

17.3 g (0.0345 mol) of 4-(3-nitrobenzoyl)phenyl 2,3,4-tri-O-acetyl-β-D-xylopyranoside, 250 ml of anhydrous methylene chloride and 125 ml of trifluoroacetic acid are introduced successively into a 500 ml round-bottomed flask placed under a stream of nitrogen. The reaction medium is cooled to 0° C. and 7.9 g (0.203 mol) of sodium tetraborohydride are added cautiously in small portions, with vigorous stirring. The reaction mixture is subsequently stirred for 2 hours at 0° C. and then for 1 hour at ambient temperature (15°–20° C.), after which it is hydrolyzed on ice. It is extracted several times with methylene chloride and the extracts are washed with water, then with a saturated solution of NaHCO$_3$ and finally with water until the pH of the washings is neutral. The organic phase is dried and then evaporated under reduced pressure. After recrystallization from diisopropyl ether, 12.24 g (yield: 73%) of the expected product are obtained.

Melting point = 105° C.

$[\alpha]_D^{20} = -25°$ (c=0.5 g/liter; ethyl acetate)

PREPARATION V

Preparation of 4-(3-nitrobenzyl)phenyl β-D-xylopyranoside (Example 2; code no. 938)

12.24 g (0.025 mol) of 4-(3-nitrobenzyl)phenyl 2,3,4-tri-O-acetyl-β-D-xylopyranoside (product of Example 37 obtained according to Preparation IV) are dissolved in 200 ml of methanol at ambient temperature (15°–20° C.), with stirring. 3 ml of 7% w/v sodium methylate solution are added. The mixture is stirred at ambient temperature until the starting material has totally disappeared (i.e. about 2 hours). Amberlite IR 120H resin is then added until the pH is neutral, after which the mixture is filtered. The filtrate thus obtained is evaporated under reduced pressure at 30°–40° C. in order to remove the methanol; the evaporation residue is then recrystallized from isopropanol to give 6.93 g (yield: 77%) of the expected product.

Melting point = 139° C.

$[\alpha]_D^{20} = -24.4°$ (c=0.5 g/liter; MeOH)

PREPARATION VI

Preparation of 4-(benzyl)phenyl 2,3,4-tri-O-acetyl-β-D-xylopyranoside (Example 68)

By following the procedure described in Preparation II, starting from 20 g of 4-(benzoyl)phenyl 2,3,4-tri-O-acetyl-β-D-xylopyranoside, 13 g (yield: 67%) of the expected product are obtained.

Melting point = 112° C.

$[\alpha]_D^{20} = -27°$ (c=0.5 g/liter; ethyl acetate)

PREPARATION VII

Preparation of 4-(benzyl)phenyl β-D-xylopyranoside (Example 33; code no. 939)

By following the procedure described in Preparation III, starting from 12 g of 4-(benzyl)phenyl 2,3,4-tri-O-acetyl-β-D-xylopyranoside, 3.13 g of the expected product are obtained.

Melting point = 160° C.

$[\alpha]_D^{20} = -28°$ (c=0.5 g/liter; MeOH)

PREPARATION VIII

Preparation of 4-(4-methylthiobenzyl)phenyl β-D-xylopyranoside (Example no. 85; code no. 887)

Preparation of 4-(4-methylthiobenzoyl)phenyl 2,3,4-tri-O-acetyl-β-D-xylopyranoside 18 g (0.0736 mol) of (4-hydroxyphenyl)(4-methythiophenyl)methanone are dissolved in 500 cm$^3$ of acetonitrile. With protection from the light, 21 g (0.088 mol) of silver oxide are introduced, the mixture is stirred for 15 minutes and 30 g (0.088 mol) of acetobromoxylose are then added. The reaction medium is stirred for three hours. It is then filtered and the filtrate is extracted with methylene chloride. The organic phase obtained is washed with 1N sodium hydroxide solution and then with water until the pH of the washings is neutral, after which it is dried over magnesium sulfate and evaporated. The evaporation residue is crystallized by the addition of ether. This gives 22.3 g of the expected product (yield: 60.16%).

Melting point = 132° C.

Preparation of 4-(4-methylthiobenzyl)phenyl 2,3,4-tri-O-acetyl-β-D-xylopyranoside (Example no. 86)

By following the procedure described in Preparation II, starting from 4-(4-methylthiobenzoyl)phenyl 2,3,4-tri-O-acetyl-β-D-xylopyranoside, the product of Example no. 86 is obtained in the form of an oil.

Preparation of the product of Example no. 85

By following the procedure described in Preparation II, starting from 6 g (0.012 mol) of 4-(4-methylthiobenzoyl)phenyl 2,3,4-tri-O-acetyl-β-D-xylopyranoside (product of Example 86), 3.9 g (yield: 86%) of the expected product are obtained after recrystallization from an ethanol/water mixture.

Melting point = 140° C.

$[\alpha_n^{20}] = -26°$ (c=0.5 g/liter; methanol)

PREPARATION IX

Preparation of 4-(4-methylsulfinylbenzyl)phenyl β-D-xylopyranoside (Example 87; code no. 909)

14.6 g (0.0403 mol) of 4-(4-methylthiobenzyl)phenyl β-D-xylopyranoside (product of Example 85; code no. 887) are introduced into 400 ml of methanol.

6.94 g (0.0403 mol) of m-chloroperoxybenzoic acid (MCPBA) are then added to the solution obtained and the mixture is left at ambient temperature for 12 hours, with stirring. The total disappearance of the starting material is determined by TLC (eluent: toluene/methanol 3:1). The reaction medium is evaporated. The acid is extracted with ether and the product precipitates. The precipitate obtained is filtered off and washed with ether in order to remove any traces of MCPBA. The ether phase is washed with water in order to recover all the expected product. The aqueous phase thus obtained is combined with the crystals. This gives a syrup which is crystallized from an isopropyl alcohol/ether mixture and the crystals obtained are then recrystallized from isopropyl alcohol. This gives 7.8 g of the expected product (yield: 51%).

Melting point = 163° C.

$[\alpha]_D^{20} = 20°$ (c=0.5 g/liter; methanol)

PREPARATION X

Preparation of 4-(4-mesylbenzyl)phenyl 2,3,4,5-tetra-O-acetyl-β-D-glucopyranoside (Example 92)

By following the procedure described in Preparation II, starting from 11.1 g (0.0183 mol) of 4-(4-mesylbenzoyl)phenyl 2,3,4,5-tetra-O-acetyl-β-D-glucopyranoside, 10.44 g of the expected product are obtained in the form of an amorphous solid (yield: 96%).

PREPARATION XI

Preparation of 4-(4-mesylbenzyl)phenyl
β-D-glucopyranoside (Example 91; code no. 1059)

By following the procedure described in Preparation III, starting from 8.1 g (0.0136 mol) of 4-(4-mesylbenzyl)phenyl tetra-O-acetyl-β-D-glucopyranoside, 4.9 g of the expected product are obtained in the form of an amorphous yellow powder by lyophilization (yield: 84%).

$[\alpha]_D^{20} = -41°$ (c=0.5; CH$_3$OH)

PREPARATION XII

Preparation of 4-(4-mesylbenzyl)phenyl
3,4,5-tri-O-acetyl-β-D-N-acetylglucosaminopyranoside (Example 94)

By following the procedure described in Preparation II, starting from 5 g (0.0086 mol) of 4-(4-mesylbenzoyl)-phenyl 2,3,4-tri-O-acetyl-β-D-N-acetylglucoaminopyranoside, 4 g of the expected product are obtained in the form of an amorphous solid (yield: 83%).

PREPARATION XIII

Preparation of 4-(4-mesylbenzyl)phenyl
β-D-N-acetylglucosaminopyranoside (Example 93; code no. 1088)

By following the procedure described in Preparation III, starting from 3.9 g (0.0069 mol) of 4-(4-mesylbenzyl)phenyl 3,4,5-tri-O-acetyl-β-D-N-acetylglucosaminopyranoside, 2.21 g of the expected product are obtained (yield: 73.6%).

Melting point=156° C.

$[\alpha]_D^{20} = +7°$ (c=0.5; CH$_3$OH)

PREPARATION XIV

Preparation of 4-(4-mesylbenzoyl)phenyl
2,3,4-tri-O-acetyl-β-D-xylopyranoside (Example 90)

Preparation of (4-hydroxyphenyl)(4-mesylphenyl)-methanone 25 g (0.102 mol) of (4-hydroxyphenyl)(4-methylthiophenyl)methanone are dissolved in 500 ml of methanol. 58 g (0.34 mol) of metachloroperoxybenzoic acid (MCPBA) are added. The reaction medium is then heated to 40° C. and left for 48 hours, with stirring. The methanol is then evaporated off and the reaction medium is taken up with ethyl acetate. This organic phase is washed with water until the pH of the washings is neutral, and then dried over magnesium sulfate and evaporated. 26.1 g of a yellow solid are obtained (yield: 93%).

Preparation of 4-(4-mesylbenzoyl)phenyl 2,3,4-tri-O-acetyl-β-D-xylopyranoside

Under a nitrogen atmosphere and with protection from the light, 26 g (0.094 mol) of (4-hydrophenyl)-(4-mesylphenyl)methanone are partially dissolved in 600 ml of anhydrous methylene chloride. 47.3 g (0.14 mol) of acetobromoxylose, 76.5 g (0.56 mol) of ZnCl$_2$ and 19.8 g (0.11 mol) of silver imidazolate are then added successively. This gives a yellow solution which is heated at 40° C. for 12 hours, with mechanical stirring. The reaction medium is then filtered and the filtrate is washed with 1 liter of methylene chloride. The organic phase is subsequently washed with 1N hydrochloric acid, then with water, then with 4% sodium hydroxide solution and again with water until the pH of the washings is neutral. After drying over magnesium sulfate, the methylene chloride is evaporated off to give 49.9 g of a viscous yellow syrup (yield: 98%).

Preparation of 4-(mesylbenzoyl)phenyl 2,3,4-tri-O-acetyl-β-D-xylopyranoside (Example 90)

49.9 g (0.094 mol) of 4-(4-mesylbenzoyl)phenyl 2,3,4-tri-O-acetyl-β-D-xylopyranoside, 500 ml of anhydrous methylene chloride and 250 ml of trifluoroacetic acid are introduced successively into a 2 liter round-bottomed flask placed under a stream of nitrogen. The color of the reaction medium changes from yellow to orange. The reaction medium is cooled and kept at 0° C., with stirring, and 18 g (0.47 mol) of sodium tetraborohydride are added in small portions. The mixture is then stirred for 12 hours, the temperature being allowed to rise gradually. The reaction mixture is then hydrolyzed on ice and extracted several times with methylene chloride and the extracts are washed with water, then with a sodium bicarbonate solution and finally with water until the pH of the washings is neutral. The organic phase obtained is dried over magnesium sulfate and then evaporated under reduced pressure. This gives 40.4 g of the expected product (yield: 83%).

PREPARATION XV

Preparation of 4-(4-mesylbenzyl)phenyl
β-D-xylopyranoside (Example 89; code no. 1008)

20 g (0.038 mol) of 4-(4-mesylbenzyl)phenyl 2,3,4-tri-O-acetyl-β-D-xylopyranoside are dissolved in 350 ml of methanol at ambient temperature. 5.7 ml of 7% w/v sodium methylate solution are added. The mixture is stirred at ambient temperature until the starting material has completely disappeared (1 hour 30 minutes). Amberlite IR 120H resin is then added until the pH is neutral, after which the mixture is filtered. The filtrate obtained is evaporated under reduced pressure at 40° C. to give 14.6 g of a syrup which crystallizes on the addition of water. The crystals are filtered off and the product obtained is then recrystallized from an isopropyl alcohol/isopropyl ether mixture. This gives 8.73 g of the expected product (yield: 58%).

$[\alpha]_D^{19} = -10°$ (c=0.5; MeOH)

Without implying a limitation, a number of compounds of the formula I according to the invention have been collated in Table I below (where the position of the substituents has been assigned arbitrarily, the vertices of the phenyl nuclei being numbered from the central CH$_2$ group).

Table II below summarizes the physical characteristics of the compounds according to the invention and Table III below summarizes the results of the tests (toxicity, hypocholesterolemic activity) undertaken on a number of products according to the invention. The experimental protocols used are as follows.

Acute toxicity

The acute toxicity was studied by intraperitoneal administration to mice. It is expressed in the form of LD$_{50}$ (lethal dose causing the death of half of the animals) or LD$_0$ (maximum non-lethal dose).

Hypocholesterolemic activity

The hypocholesterolemic activity was studied on male Wistar rats (weighing about 200 to 220 g). Groups of 10 rats per product and per dose are fasted the day before the experiment. The products to be tested are administered in gum water (30 g/liter of gum arabic) at times $T=0$ and $T=+7$ hours. The cholesterol level in the plasma is measured at times $T=0$ and $T=+24$ hours and the percentage variation between $T=0$ and $T=+24$ hours is then calculated for the treated groups and the control groups. The results are collated in Table III.

In particular, the products of the formula (I) can be administered orally in the form of gelatine capsules or coated or non-coated tablets each containing 0.05 to 1.5 g of at least one compound of the formula (I) as the active principle, and preferably 0.1 to 0.9 g, on the one hand, and by injection in the form of solutions containing from 0.05 to 0.5 g of active principle in 2 to 10 cm³ of distilled water, on the other. These galenical forms can be administered at a rate of 1 to 4 doses per day.

TABLE I

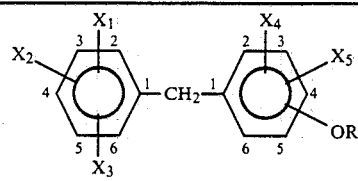

| Example | Code No. | $X_1$ | $X_2$ | $X_3$ | $X_4$ | $X_5$ | Position of OR | R |
|---|---|---|---|---|---|---|---|---|
| 1 | 646 | 4-$NO_2$ | H | H | H | H | para | $\beta$-D-xyl |
| 2 | 938 | 3-$NO_2$ | H | H | H | H | para | $\beta$-D-xyl |
| 3 | 1090 | 4-$NO_2$ | H | H | H | H | para | $\beta$-D-glu—NHAc |
| 4 | 1311 | 4-$NO_2$ | H | H | H | H | para | $\beta$-D-gal |
| 5 | 1346 | 4-$NO_2$ | H | H | H | H | para | $\alpha$-L-rham |
| 6 | 1244 | 4-$NO_2$ | H | H | H | H | para | $\alpha$-L-arab |
| 7 | 1089 | 2-Cl | H | H | H | H | para | $\beta$-D-xyl |
| 8 | 1208 | 3-Cl | H | H | H | H | para | $\beta$-D-xyl |
| 9 | 940 | 4-Cl | H | H | H | H | para | $\beta$-D-xyl |
| 10 | 1211 | 4-Br | H | H | H | H | para | $\beta$-D-xyl |
| 11 | 1091 | 4-$CH_3$ | H | H | H | H | para | $\beta$-D-xyl |
| 12 | 1092 | 2-$CH_3$ | H | H | H | H | para | $\beta$-D-xyl |
| 13 | 1207 | 3-$CH_3$ | H | H | H | H | para | $\beta$-D-xyl |
| 14 |  | 4t-Bu | H | H | H | H | para | $\beta$-D-xyl |
| 15 | 1133 | 4-$OCH_3$ | H | H | H | H | para | $\beta$-D-xyl |
| 16 |  | 2-$OCH_3$ | H | H | H | H | para | $\beta$-D-xyl |
| 17 | 1135 | 3-$OCH_3$ | H | H | H | H | para | $\beta$-D-xyl |
| 18 | 1305 | 4-$CF_3$ | H | H | H | H | para | $\beta$-D-xyl |
| 19 | 1134 | 4-$NH_2$ | H | H | H | H | para | $\beta$-D-xyl |
| 20 | 1352 | 4-$N(CH_3)_2$ | H | H | H | H | para | $\beta$-D-xyl |
| 21 |  | 4-NHi-Pr | H | H | H | H | para | $\beta$-D-xyl |
| 22 |  | 2-$NH_2$ | H | H | H | H | para | $\beta$-D-xyl |
| 23 | 1252 | 3-$NH_2$ | H | H | H | H | para | $\beta$-D-xyl |
| 24 |  | 4-$NO_2$ | H | H | H | H | meta | $\beta$-D-xyl |
| 25 | 1364 | 4-$NO_2$ | H | H | H | H | ortho | $\beta$-D-xyl |
| 26 | 1136 | 2-Cl | 4-Cl | H | H | H | para | $\beta$-D-xyl |
| 27 | 1197 | 2-$CH_3$ | 4-$CH_3$ | 6-$CH_3$ | H | H | para | $\beta$-D-xyl |
| 28 |  | 3-$OCH_3$ | 4-$OCH_3$ | 5-$OCH_3$ | H | H | para | $\beta$-D-xyl |
| 29 | 1206 | 4-OH | H | H | H | H | para | $\beta$-D-xyl |
| 30 | 1209 | 4-$CH_3$ | H | H | 3-$CH_3$ | 5-$CH_3$ | para | $\beta$-D-xyl |
| 31 |  | 4-$NO_2$ | H | H | 3-$OCH_3$ | 5-$OCH_3$ | para | $\beta$-D-xyl |
| 32 |  | H | H | H | 2-$CH_3$ | H | para | $\beta$-D-xyl |
| 33 | 939 | H | H | H | H | H | para | $\beta$-D-xyl |
| 34 | 1328 | H | H | H | 3-$NO_2$ | H | para | $\beta$-D-xyl |
| 35 |  | 4-$NO_2$ | H | H | 3-Cl | H | ortho | $\beta$-D-xyl |
| 36 |  | 4-$NO_2$ | H | H | H | H | para | $(OAc)_3$—$\beta$-D-xyl |
| 37 |  | 3-$NO_2$ | H | H | H | H | para | $(OAc)_3$—$\beta$-D-xyl |
| 38 |  | 4-$NO_2$ | H | H | H | H | para | $(OAc)_3$—$\beta$-glu—NHAc |
| 39 |  | 4-$NO_2$ | H | H | H | H | para | $(OAc)_4$—$\beta$-D-gal |
| 40 | 1245 | 4-$NO_2$ | H | H | H | H | para | $(OAc)_3$—$\alpha$-L-rham |
| 41 |  | 4-$NO_2$ | H | H | H | H | para | $(OAc)_3$—$\alpha$-L-arab |
| 42 |  | 2-Cl | H | H | H | H | para | $(OAc)_3$—$\beta$-D-xyl |
| 43 |  | 3-Cl | H | H | H | H | para | $(OAc)_3$—$\beta$-D-xyl |
| 44 |  | 4-Cl | H | H | H | H | para | $(OAc)_3$—$\beta$-D-xyl |
| 45 |  | 4-Br | H | H | H | H | para | $(OAc)_3$—$\beta$-D-xyl |
| 46 |  | 4-$CH_3$ | H | H | H | H | para | $(OAc)_3$—$\beta$-D-xyl |
| 47 |  | 2-$CH_3$ | H | H | H | H | para | $(OAc)_3$—$\beta$-D-xyl |
| 48 |  | 3-$CH_3$ | H | H | H | H | para | $(OAc)_3$—$\beta$-D-xyl |
| 49 |  | 4-t-Bu | H | H | H | H | para | $(OAc)_3$—$\beta$-D-xyl |
| 50 |  | 4-$OCH_3$ | H | H | H | H | para | $(OAc)_3$—$\beta$-D-xyl |
| 51 |  | 2-$OCH_3$ | H | H | H | H | para | $(OAc)_3$—$\beta$-D-xyl |
| 52 |  | 3-$OCH_3$ | H | H | H | H | para | $(OAc)_3$—$\beta$-D-xyl |
| 53 |  | 4-$CF_3$ | H | H | H | H | para | $(OAc)_3$—$\beta$-D-xyl |
| 54 |  | 4-$NH_2$ | H | H | H | H | para | $(OAc)_3$—$\beta$-D-xyl |
| 55 |  | 4-$N(CH_3)_2$ | H | H | H | H | para | $(OAc)_3$—$\beta$-D-xyl |
| 56 |  | 4-NHi-Pr | H | H | H | H | para | $(OAc)_3$—$\beta$-D-xyl |
| 57 |  | 2-$NH_2$ | H | H | H | H | para | $(OAc)_3$—$\beta$-D-xyl |

TABLE I-continued

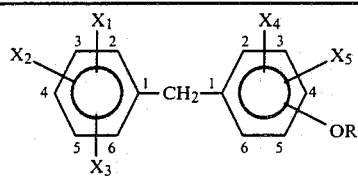

| Example | Code No. | $X_1$ | $X_2$ | $X_3$ | $X_4$ | $X_5$ | Position of OR | R |
|---|---|---|---|---|---|---|---|---|
| 58 |  | 3-$NH_2$ | H | H | H | H | para | $(OAc)_3$—β-D-xyl |
| 59 |  | 4-$NO_2$ | H | H | H | H | meta | $(OAc)_3$—β-D-xyl |
| 60 |  | 4-$NO_2$ | H | H | H | H | ortho | $(OAc)_3$—β-D-xyl |
| 61 |  | 2-Cl | 4-Cl | H | H | H | para | $(OAc)_3$—β-D-xyl |
| 62 | 1199 | 2-$CH_3$ | 4-$CH_3$ | 6-$CH_3$ | H | H | para | $(OAc)_3$—β-D-xyl |
| 63 |  | 3-$OCH_3$ | 4-$OCH_3$ | 5-$OCH_3$ | H | H | para | $(OAc)_3$—β-D-xyl |
| 64 |  | 4-OH | H | H | H | H | para | $(OAc)_3$—β-D-xyl |
| 65 |  | 4-$NO_2$ | H | H | 3-$CH_3$ | 5-$CH_3$ | para | $(OAc)_3$—β-D-xyl |
| 66 |  | 4-$OCH_3$ | H | H | 3-$OCH_3$ | 5-$OCH_3$ | para | $(OAc)_3$—β-D-xyl |
| 67 |  | H | H | H | 2-$CH_3$ | H | para | $(OAc)_3$—β-D-xyl |
| 68 |  | H | H | H | H | H | para | $(OAc)_3$—β-D-xyl |
| 69 |  | H | H | H | 3-$NO_2$ | H | para | $(OAc)_3$—β-D-xyl |
| 70 |  | 4-$NO_2$ | H | H | 5-Cl | H | ortho | $(OAc)_3$—β-D-xyl |
| 71 | 1205 | 4-$NO_2$ | H | H | H | H | para | β-D-glu |
| 72 |  | 4-$NO_2$ | H | H | H | H | para | $(OAc)_4$—β-D-glu |
| 73 |  | 4-$CH_3$ | H | H | 3-Cl | 5-Cl | para | β-D-xyl |
| 74 |  | 4-$CH_3$ | H | H | 3-Cl | 5-Cl | para | $(OAc)_3$—β-D-xyl |
| 75 | 1354 | 4-Cl | H | H | H | H | meta | β-D-xyl |
| 76 |  | 4-Cl | H | H | H | H | meta | $(OAc)_3$—β-D-xyl |
| 77 | 1353 | H | H | H | H | H | meta | β-D-xyl |
| 78 |  | H | H | H | H | H | meta | $(OAc)_3$—β-D-xyl |
| 79 | 1212 | H | H | H | 3-$CH_3$ | H | para | β-D-xyl |
| 80 |  | H | H | H | 3-$CH_3$ | H | para | $(OAc)_3$—β-D-xyl |
| 81 |  | 4-$CH_3$ | H | H | 3-$CH_3$ | 5-$CH_3$ | para | $(OAc)_3$—β-D-xyl |
| 82 | 1198 | 4-$NO_2$ | H | H | 3-$CH_3$ | 5-$CH_3$ | para | β-D-xyl |
| 83 |  | 4-NHAc | H | H | H | H | meta | β-D-xyl |
| 84 |  | 4-NHAc | H | H | H | H | meta | $(OAc)_3$—β-D-xyl |
| 85 | 887 | 4-$SCH_3$ | H | H | H | H | para | β-D-xyl |
| 86 |  | 4-$SCH_3$ | H | H | H | H | para | $(OAc)_3$—β-D-xyl |
| 87 | 909 | 4-$SOCH_3$ | H | H | H | H | para | β-D-xyl |
| 88 |  | 4-$SOCH_3$ | H | H | H | H | para | $(OAc)_3$—β-D-xyl |
| 89 | 1008 | 4-$SO_2CH_3$ | H | H | H | H | para | β-D-xyl |
| 90 |  | 4-$SO_2CH_3$ | H | H | H | H | para | $(OAc)_3$—β-D-xyl |
| 91 | 1059 | 4-$SO_2CH_3$ | H | H | H | H | para | β-D-glu |
| 92 |  | 4-$SO_2CH_3$ | H | H | H | H | para | $(OAc)_4$—β-D-glu |
| 93 | 1088 | 4-$SO_2CH_3$ | H | H | H | H | para | β-D-gluNHAc |
| 94 |  | 4-$SO_2CH_3$ | H | H | H | H | para | $(OAc)_3$—β-D-gluNHAc |

TABLE II

PHYSICAL CONSTANTS

| Example | Code no. | Melting point °C. | $[\alpha]_D^{20}$ | C: g/liter |
|---|---|---|---|---|
| 1 | 646 | 166 | −21 | C = 0.5 $CH_3OH$ |
| 2 | 938 | 139 | −24.4 | C = 0.5 $CH_3OH$ |
| 3 | 1090 | 251 | −30 | C = 0.5 DMF |
| 4 | 1311 | 162 | −29 | C = 0.5 $CH_3OH$ |
| 5 | 1346 | 58 | −89 | C = 0.5 $CH_3OH$ |
| 6 | 1244 | 99 | 0 | C = 0.5 $CH_3OH$ |
| 7 | 1089 | 183 | −27 | C = 0.5 $CH_3OH$ |
| 8 | 1208 | 153 | −24 | C = 0.5 $CH_3OH$ |
| 9 | 940 | 149 | −25 | C = 0.5 $CH_3OH$ |
| 10 | 1211 | 162 | −21 | C = 0.5 $CH_3OH$ |
| 11 | 1091 | 165 | −28 | C = 0.5 $CH_3OH$ |
| 12 | 1092 | 175 | −28 | C = 0.5 $CH_3OH$ |
| 13 | 1207 | 154 | −26 | C = 0.5 $CH_3OH$ |
| 15 | 1133 | 153 | −28 | C = 0.5 $CH_3OH$ |
| 17 | 1135 | 138 | −29 | C = 0.5 $CH_3OH$ |
| 18 | 1305 | 158 | −23 | C = 0.5 $CH_3OH$ |
| 19 | 1134 | 166 | −30 | C = 0.5 $CH_3OH$ |
| 20 | 1352 | 160 | −26 | C = 0.5 $CH_3OH$ |
| 23 | 1252 | 188 | −27 | C = 0.5 $CH_3OH$ |
| 25 | 1364 | 197 | −43 | C = 0.5 $CH_3OH$ |
| 26 | 1136 | 158 | −26 | C = 0.5 $CH_3OH$ |
| 27 | 1197 | 222 | −21 | C = 0.5 $CH_3OH$ |
| 29 | 1206 | 175 | −27 | C = 0.5 $CH_3OH$ |
| 30 | 1209 | 150 | +22 | C = 0.5 $CH_3OH$ (*) |
| 33 | 939 | 160 | −28 | C = 0.5 $CH_3OH$ |
| 34 | 1328 | amorphous | −43 | C = 0.5 $CH_3OH$ |
| 36 |  | oil | −40 | C = 0.5 $CHCl_3$ |
| 37 |  | 105 | −25 | C = 0.5 $CH_3COOC_2H_5$ |
| 38 |  | 227 | −7 | C = 0.5 $CH_3COOC_2H_5$ |
| 39 |  | 118 | +5 | C = 0.5 $CH_3COOC_2H_5$ |
| 40 | 1245 | 62 | −64 | C = 0.5 $CH_3COOC_2H_5$ |
| 41 |  | 70 | +22 | C = 0.5 $CH_3OH$ |
| 42 |  | 85 | −21 | C = 0.5 $CH_3COOC_2H_5$ |
| 43 |  | 119 | −19 | C = 0.5 $CH_3COOC_2H_5$ |
| 44 |  | 101 | −19 | C = 0.5 $CH_3COOC_2H_5$ |
| 45 |  | 112 | −17 | C = 0.5 $CH_3COOC_2H_5$ |
| 46 |  | 114 | −22 | C = 0.5 $CH_3COOC_2H_5$ |
| 47 |  | 108 | −22 | C = 0.5 $CH_3COOC_2H_5$ |
| 48 |  | 90 | −23 | C = 0.5 $CH_3COOC_2H_5$ |
| 50 |  | 80 | −21 | C = 0.5 $CH_3COOC_2H_5$ |
| 52 |  | 108 | −5 | C = 0.5 $CH_3COOC_2H_5$ |
| 53 |  | 82 | −21 | C = 0.5 $CH_3COOC_2H_5$ |
| 55 |  | 145 | −21 | C = 0.5 $CH_3COOC_2H_5$ |
| 58 |  | 69 | −21 | C = 0.5 $CH_3COOC_2H_5$ |
| 60 |  | oil | −40 | C = 0.5 $CH_3COOC_2H_5$ |
| 61 |  | 99 | −17 | C = 0.5 $CH_3COOC_2H_5$ |
| 62 | 1199 | 133 | −16 | C = 0.5 $CH_3COOC_2H_5$ |
| 64 |  | 110 | −21 | C = 0.5 $CH_3COOC_2H_5$ |
| 65 |  | 73 | +9 | C = 0.5 $CH_3COOC_2H_5$ (*) |
| 68 |  | 112 | −27 | C = 0.5 $CH_3COOC_2H_5$ |

TABLE II-continued
PHYSICAL CONSTANTS

| Example | Code no. | Melting point °C. | $[\alpha]_D^{20}$ | C: g/liter | |
|---|---|---|---|---|---|
| 69 | | 140 | −46 | C = 0.5 | $CH_3COOC_2H_5$ |
| 71 | 1205 | (**) | −39 | C = 0.5 | $CH_3OH$ |
| 72 | | 128 | −17 | C = 0.5 | $CH_3COOC_2H_5$ |
| 75 | 1354 | 134 | −35 | C = 0.5 | $CH_3OH$ |
| 76 | | 99 | −44 | C = 0.5 | $CH_3COOC_2H_5$ |
| 77 | 1353 | 141 | −38 | C = 0.5 | $CH_3OH$ |
| 78 | | 110 | −46 | C = 0.5 | $CH_3COOC_2H_5$ |
| 79 | 1212 | 126 | −31 | C = 0.5 | $CH_3OH$ |
| 80 | | 87 | −29 | C = 0.5 | $CH_3COOC_2H_5$ |
| 81 | | 63 | +3 | C = 0.5 | $CH_3COOC_2H_5$ (*) |
| 82 | 1109 | 135 | +25 | C = 0.5 | $CH_3OH$ (*) |
| 83 | | 171 | −28 | C = 0.5 | $CH_3OH$ |
| 84 | | oil | −26 | C = 0.5 | $CH_3OH$ |
| 85 | 887 | 140 | −26 | C = 0.5 | $CH_3OH$ |
| 87 | 909 | 163 | −20 | C = 0.5 | $CH_3OH$ |
| 89 | 1008 | 146 | −10 | C = 0.5 | $CH_3OH$ |
| 91 | 1059 | amorphous compound | −41 | C = 0.5 | $CH_3OH$ |
| 93 | 1088 | 156 | +7 | C = 0.5 | $CH_3OH$ |

(*) mixture of diastereoisomers
(**) double melting point: 84 and 135

TABLE III

| Example (+) | Code No. | $LD_0$, $LD_{50}$ mg/kg i.p. | dose administered p.o. (mg/kg) | % Variation in the cholesterol level, variation in the subject treated (%) (*) |
|---|---|---|---|---|
| 1 | 646 | $LD_{50}$ = 650 | 65 | −39 |
| 2 | 938 | $LD_0$ > 800 | 100 | −27 |
| 3 | 1090 | $LD_0$ > 800 | 100 | −42 |
| 4 | 1311 | $LD_0 \geqq$ 900 | 100 | −33 |
| 5 | 1346 | | 100 | −7 |
| 6 | 1244 | $LD_0 \geqq$ 900 | 100 | −29 |
| 7 | 1089 | $LD_0$ > 800 | 100 | −20 |
| 8 | 1208 | $LD_{50} \geqq$ 800 | 100 | −37 |
| 9 | 940 | $LD_0$ > 800 | 100 | −37 |
| 10 | 1211 | $LD_0 \geqq$ 900 | 100 | −39 |
| 11 | 1091 | $LD_0$ > 800 | 100 | −19 |
| 12 | 1092 | $LD_0$ > 800 | 100 | −28 |
| 13 | 1207 | $LD_0 \geqq$ 800 | 100 | −24 |
| 15 | 1133 | $LD_0$ > 800 | 100 | −47 |
| 17 | 1135 | $LD_0$ > 1000 | 100 | −50 |
| 18 | 1305 | $LD_{50}$ > 900 | 100 | −17 |
| 19 | 1134 | $LD_0$ > 800 | 100 | −29 |
| 20 | 1352 | | 100 | −22 |
| 23 | 1252 | $LD_0 \geqq$ 900 | 100 | −28 |
| 26 | 1136 | $LD_{50}$ = 640 | 100 | −8 |
| 27 | 1197 | $LD_0 \geqq$ 800 | 100 | −13 |
| 29 | 1206 | $LD_0 \geqq$ 800 | 100 | −37 |
| 30 | 1209 | $LD_{50}$ = 630 | 100 | −12 |
| 33 | 939 | $LD_0$ > 800 | 100 | −38 |
| 34 | 1328 | $LD_{50}$ = 250 | 25 | −15 |
| 62 | 1199 | $LD_0$ > 900 | 100 | −18 |
| 71 | 1205 | $LD_0 \geqq$ 900 | 65 | −21 |
| 75 | 1354 | | 100 | −43 |
| 77 | 1353 | | 100 | −25 |
| 79 | 1212 | $LD_{50}$ = 320 | 30 | −37 |
| 82 | 1198 | $LD_0$ > 800 | 100 | −11 |
| 85 | 887 | $LD_0$ > 800 | 100 | −23 |
| 89 | 1008 | $LD_{50}$ = 450 | 45 | −30 |
| 91 | 1059 | $LD_0$ > 800 | 100 | −40 |
| 93 | 1088 | $LD_0$ > 800 | 100 | −36 |

(*) not corrected for the variation in the control group
(+) products preferred from the point of view of the hypocholesterolemic activity

What is claimed is:

1. Benzyl-phenyl xylosides selected from the group consisting of:
  (i) compounds corresponding to general formula:

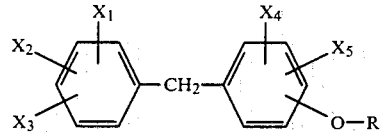

in which:

$X_1$, $X_2$, $X_3$, $X_4$ and $X_5$, which are identical or different, each represent a hydrogen atom, a halogen atom, a $C_1$–$C_4$ alkyl group, a $C_1$–$C_4$ alkyl group substituted by one or more halogen atoms, an OH group, a $C_1$–$C_4$ alkoxy group, a $C_1$–$C_4$ alkoxy group substituted by one or more halogen atoms, a nitro group, a group NR'R" (in which R' and R", which are identical or different, each represent the hydrogen atom, a $C_1$–$C_4$ alkyl group or an acetyl group) a methylthio group, a methylsulfinyl group or a mesyl group, and —R represents a radical xylose substituted with at least one acyl group (ii) their acid addition salts in cases where at least one of the groups $X_1$, $X_2$, $X_3$, $X_4$, $X_5$ represents the group NR'R".

2. Benzyl-phenyl xylosides as claimed in claim 1, wherein $X_1$, $X_2$, $X_3$, $X_4$ and $X_5$ which can be identical or different, each represent H, Cl, Br, $CH_3$, $CF_3$, OH, $OCH_3$, $NO_2$, $NH_2$, $N(CH_3)_2$, $SCH_3$, $SOCH_3$ or $SO_2CH_3$ and R represents a radical xyloside substituted with at least one acetyl group.

3. 4-(4-Nitrobenzyl)phenyl beta-D-xylopyranoside.

4. 4-(4-Chlorobenzyl) phenyl beta-D-xylopyranoside.

5. 3-(4-Chlorobenzyl) phenyl beta-D-xylopyranoside.

6. 4-(4-Mesylbenzyl)phenyl beta-D-xylopyranoside.

7. A therapeutic composition containing in association with a physiologically acceptable excipient, an effective hypocholesterolemic and hypolipidemic treating amount of a compound according to claim 1.

8. A method for the preparation of a benzyl-phenylxyloside of the formula I as claimed in claim 1, which comprises reducing a compound belonging to the family of the benzoylphenyl osides and α-hydroxybenzylphenyl osides of the formula

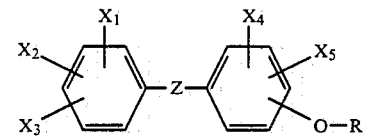

in which Z is CO or CHOH and $X_1$, $X_2$, $X_3$, $X_4$, $X_5$ and R are defined as indicated above) by means of a reducing agent chosen from $NaBH_4$ and $KBH_4$, in trifluoroacetic acid.

9. Method as claimed in claim 8, which comprises successively
  (i) introducing the reducing agent into a mixture comprising the compound of the formula II and the trifluoroacetic acid, at a temperature below or equal to 0° C., over at least 0.5 hour, the reducing agent being in excess relative to the compound II; and
  (ii) when the said addition has ended allowing the reaction to continue for 0.5 to 12 hours at a temperature of between 0° and 20° C., with stirring.

10. A therapeutic composition containing in association with a physiologically acceptable excipient, an effective anti-thrombotic treating amount of the compound according to claim 3.

* * * * *